(12) United States Patent
Owen

(10) Patent No.: US 6,209,343 B1
(45) Date of Patent: Apr. 3, 2001

(54) PORTABLE APPARATUS FOR STORING AND/OR TRANSPORTING BIOLOGICAL SAMPLES, TISSUES AND/OR ORGANS

(75) Inventor: Donald R. Owen, New Orleans, LA (US)

(73) Assignee: Life Science Holdings, Inc., Des Plaines, IL (US)

( * ) Notice: Subject to any disclaimer, the term of this patent is extended or adjusted under 35 U.S.C. 154(b) by 0 days.

(21) Appl. No.: 09/161,919

(22) Filed: Sep. 29, 1998

(51) Int. Cl.[7] .................................................. F25D 3/08
(52) U.S. Cl. ........................ 62/457.2; 62/530; 62/457.9; 62/114; 62/201; 62/371; 62/384; 62/385; 252/67; 252/71
(58) Field of Search .................................. 62/530, 457.2, 62/457.9, 114, 201, 371, 384, 385; 252/67, 71

(56) References Cited

U.S. PATENT DOCUMENTS

| | | |
|---|---|---|
| 3,167,933 | 2/1965 | Beckman et al. . |
| 3,238,002 | 3/1966 | O'Connell et al. . |
| 3,916,804 * | 11/1975 | Noone .................................. 109/78 |
| 4,468,932 | 9/1984 | Bullard . |
| 4,821,914 | 4/1989 | Owen et al. . |
| 4,947,658 * | 8/1990 | Wheeler et al. ...................... 62/372 |
| 4,974,423 | 12/1990 | Pring . |
| 5,103,651 * | 4/1992 | Coelho et al. ........................ 62/341 |
| 5,313,848 | 5/1994 | Santin et al. . |
| 5,355,684 * | 10/1994 | Guice .................................... 62/54.2 |
| 5,375,423 | 12/1994 | Delatte . |
| 5,386,706 | 2/1995 | Bergsten et al. . |
| 5,419,139 | 5/1995 | Blum et al. . |
| 5,435,142 * | 7/1995 | Silber ..................................... 62/60 |
| 5,483,799 | 1/1996 | Dalto . |
| 5,598,713 | 2/1997 | Bartilucci . |
| 5,647,226 | 7/1997 | Scaringe et al. . |
| 5,899,088 * | 5/1999 | Purdum ................................ 62/371 |
| 5,918,478 * | 7/1999 | Bostic et al. ......................... 62/371 |
| 5,924,302 * | 7/1999 | Derifield ............................ 62/457.2 |
| 5,942,553 * | 8/1999 | Biesmans et al. .................... 521/99 |

FOREIGN PATENT DOCUMENTS

| | | |
|---|---|---|
| 644629 | 7/1962 | (CA) . |
| 1-134-398 | 8/1962 | (DE) . |
| 1-3412556 | 10/1985 | (DE) . |
| 0501061 | 9/1992 | (EP) . |
| 2-225-847 | 6/1990 | (GB) . |
| WO-A-97/17308 | 5/1997 | (WO) . |

* cited by examiner

Primary Examiner—William Doerrler
Assistant Examiner—Mark Shulman
(74) Attorney, Agent, or Firm—Oliff & Berridge, PLC (57) ABSTRACT

An apparatus that utilizes the heat transfer ability of cryogenic materials to maintain its contents at low temperatures includes a container having inner and outer shells. The inner and outer shells have a chamber formed therebetween. An insulation layer is disposed within the chamber. The inner shell is disposed within the outer shell to form a chamber for receiving therein a material for storage and/or transport therebetween. A phase change material is disposed within the storage chamber and includes cut-outs for receiving therein a cryogenic material. Alternatively, a pre-charged phase change material insert is provided in the storage chamber and/or the storage chamber is packed with a filler material pre-chilled in a cryogenic material. A lid seals the container.

60 Claims, 8 Drawing Sheets

PORTABLE APPARATUS FOR STORING AND/OR TRANSPORTING BIOLOGICAL SAMPLES, TISSUES AND/OR ORGANS

BACKGROUND OF THE INVENTION

1. Field of Invention

The present invention relates to apparatus for preserving contents stored and/or transported therein by utilizing a cryogenic material. The apparatus is particularly useful for storing and/or shipping materials, such as, for example, biological samples, tissues and/or organs.

2. Description of Related Art

Cryogenic materials have been used for the storage and preservation of perishable products, such as, for example, biological materials. The materials are stored in double-walled vacuum-insulated cylindrical containers. However, conventional storage containers do not attain a very low rate of heat transmission; that is, heat leaks from the surface exposed to ambient atmosphere to the surface exposed to the cryogenic material.

For example, U.S. Pat. No. 4,821,914 describes a cylindrical storage container which may be used to store perishable materials, such as food or biological samples, for transfer in a module by the space shuttle to a space station. As seen in FIG. 1, the container 16 is formed in two parts 18 and 20, each part having an inner shell 22 and an outer shell 24 formed of a metallic material such as steel or aluminum. The outer shell 24 is spaced from and disposed around the inner shell 22. The inner shell 22 forms a storage section 52 for receiving therein perishable materials. The space between the shells 22, 24 is filled with a getter material 46 and a continuous wrap multi-layer insulation material 44, such as a MYLAR brand polyethylene film having thin film aluminized surfaces. After the two parts of the container 18, 20 are filled with the perishable material, they are connected together and a vacuum is drawn in the space between the shells 22, 24. For more stringent temperature restrictions, the container of FIG. 3 may comprise two units 118, 118, each unit comprising inner and outer shells 122, 124 formed of a glass fiber material. All of the glass fiber material is lined with a metallic liner formed from stainless steel foil. A phase change material 144, such as paraffin wax or lithium chloride, fills the cavity between the inner shell 122 and the metallic liner 132. The phase change material is charged or frozen by filling a refrigerant cooling coil 148, disposed throughout the phase change material, with a cold gas. Connected together, a vacuum is drawn in the space between the shells 122, 124. A getter material is incorporated in the space between the respective inner and outer shells to absorb trace gases.

U.S. Pat. No. 4,974,423 discloses a cylindrical double-walled insulated container for transporting frozen materials, such as frozen biological samples. The container includes a main body 1 having two compartments 4, 8. The first compartment 4 holds the frozen material to be transported, and the second compartment 8 receives and holds the refrigerant, for example, dry ice or liquid nitrogen. The second compartment 8 encircles the first compartment 4. The container may be equipped with a temperature sensor 11 and a timer 14 from which aspects of the thermal history of the frozen material during storage in the container can be determined.

U.S. Pat. No. 3,238,002 discloses an insulated liquid nitrogen-refrigerated container 1 for shipping biological materials. The container 1 has an outer wall 2 and an inner vessel 3 disposed so as to provide an evacuable space 4 therebetween. Within the evacuable space 4, an insulating material is disposed composed of alternating layers of a metallic radiant heat barrier substance 5 and a fibrous substance 6. Within the inner vessel 3 is a specimen holder 7 formed of an integral mass of sand-lime filler that retains absorbed liquid nitrogen to cool material stored in voids in the specimen holder. The container 1 is sealed by a heat conductive plug 9. A gasket 14 is provided between a cap 15 and the outer wall 2 to seal the inner vessel 3. The cap 15 is composed of aluminum providing protection for the sealing means and, if desired, accommodating spring lock fasteners for locking the cap 15 and, in turn, the plug 9 to the outer shell 2.

U.S. Pat. No. 3,167,933 discloses a double-walled and vacuum-insulated storage container 10 for storing material at low temperatures by refrigerating the same utilizing a cryogenic fluid. The container 10 has a substantially uniform three dimensional rectangular structure. The outer shell 12 is a composite structure comprising a core 21, preferably constructed of laminated material, such as plywood or Masonite, unlaminated material, such as maple wood, or a suitable metallic honeycomb structure, which is substantially completely covered with metallic sheeting 22, preferably constructed of stainless steel. The inner vessel 14 is formed of a relatively flexible metallic material that is reinforced by cross-bridging the inner vessel walls so as to prevent excessive differential between the inner vessel interior and the surrounding evacuable insulation space 20. The container 10 is closed by an insulated aluminum cover 62. In operation, liquid nitrogen is transferred from a storage vessel into the container storage space defined by inner vessel 14. The material to be stored is then inserted into the inner vessel and immersed into the liquid nitrogen.

The above described patents are representative of various systems available for preserving perishable items. Each of these systems offers varying degrees of cooling capacity and temperature control. However, none of the above described systems offers a portable self-contained container which provides a high cooling capacity and a very low-heat leak system such as is provided by the present invention.

SUMMARY OF THE INVENTION

The present invention is an apparatus that utilizes a cryogenic material to preserve a material, such as, for example, a biological sample, tissue or organ, which is stored and/or transported therein. The apparatus utilizes the heat transfer ability of cryogenic materials to maintain the material disposed therein at a temperature within a range capable of preserving the material.

A cryogenic material is a material capable of producing low temperatures. Cryogenic materials, for example, compressed gas or solid carbon dioxide and compressed gas or liquid nitrogen, have very low subliming or boiling temperatures. They are capable of absorbing large amounts of heat to produce very low temperatures, such as, for example, temperatures around ±10° C., preferably ±5° C., more preferably ±2° C., of said subliming or boiling temperature, in adjacent materials when they change from one state to another, for example, from a liquid or solid state to a gaseous state. In addition, when a compressed cryogenic material is allowed to expand, its temperature decreases and the cryogenic material is capable of cooling adjacent materials by absorbing heat from the materials as the compressed material expands.

A system for containing a cryogenic material should have a very low rate of heat transmission to the ambient atmosphere, that is, heat leak from the surface exposed to ambient atmosphere to the surface exposed to the cryogenic material. Because of the large temperature differential, the thermal driving potential is very high. Heat leak into a cryogenic material is particularly costly and undesirable because of the large amount of work required in achieving the cryogenic temperature.

Apparatus according to the invention utilizes cryogenic materials in two ways. Within the apparatus to maintain the temperature therein within a desired range capable of preserving the material disposed therein. Additionally and/or alternatively, to pre-chill another the material, which then maintains the temperature within a desired range capable of preserving the material disposed therein. The apparatus are more efficient than conventional containers as they sufficiently reduce heat transmission through their walls while maintaining their contents within the desired temperature range. Further, apparatus according to the invention can maintain their internal temperature. In addition, apparatus according to the invention may be equipped with time and temperature monitoring apparatus for recording the temperature history of the time during which the material is being stored and/or transported to provide the user with an accurate record thereof.

BRIEF DESCRIPTION OF THE DRAWINGS

These and other aspects and advantages of the invention will become apparent from the following detailed description of embodiments when taken in conjunction with the accompanying drawings, in which.

DETAILED DESCRIPTION OF PREFERRED EMBODIMENTS

For a general understanding of the features of the invention, reference is made to the drawings. In the drawings, like reference numerals have been used throughout to designate like elements.

The present invention provides an apparatus for storing materials, for example biological samples, tissues and/or organs, at controlled temperatures. The apparatus according to one embodiment of the invention includes a container having inner and outer shells. The inner and outer shells are preferably three dimensionally rectangular in shape to maximize space; however, cylindrical and other shapes may be appropriate. The outer shell includes inner and outer shell members, preferably formed of a material having low thermal conductivity and high resistivity to low temperature, such as, for example, a carbon/epoxy composite or e-glass. Formed between the inner and outer shell members of the outer shell is a first chamber with an insulation layer disposed therein. The first chamber is preferably fitted with means to permit its evacuation.

The insulation layer is preferably formed of at least one layer of an insulation material, such as, for example, an aerogel preferably disposed within a layer of metalized polyethylene. The aerogel retards heat leak. The metalized polyethylene provides very low permeability to most gases, and good resistance to cracking. The aerogel is preferably silica aerogel because its base, silicon dioxide, has a tetrahedral structure conducive to forming strong molecular bonds and is nonflammable; however, other types of aerogel may also be appropriate. A getter material may also be provided in the insulation layer. Preferred getter materials include titanium; however, any getter material that absorbs trace gases within a vacuum may be used. Formed in the outer shell member of the outer shell is a vacuum port to allow a vacuum to be connected to the chamber formed between the inner and outer shell members of the outer shell.

The inner shell is disposed within the outer shell. The inner shell is preferably formed of a material having a high thermal conductivity and high resistivity to low temperature, such as, for example, aluminum oxide epoxy, aluminum or stainless steel. Formed between the inner and outer shells is a second chamber. A phase change material having cut-outs for receiving a cryogenic material, such as, for example, compressed gaseous or liquid nitrogen or compressed gaseous or solid carbon dioxide is disposed within the second chamber. Preferred phase change materials include paraffin wax and lithium chloride. Conductive material such as aluminum oxide powder may be added to the phase change material to increase the speed by which the phase change material changes phase when exposed to the compressed cryogenic material. Formed within the inner shell is a third chamber for receiving the material for storage and/or transport.

The container is closed by a lid. The lid preferably includes a top portion and an inner portion. The lid may seal only the third chamber or both the second and third chambers.

The container may also include a gap disposed between the inner shell and the phase change material. Fluid pathways disposed in the lid provide fluid communication between the gap and the third chamber when the container is closed by the lid. A temperature sensor may be included for sensing the temperature within the third chamber. Fluid communication between the gap and the third chamber may be controlled by shutter mechanisms. A fan or other pumping mechanism (hereinafter "fan") may be provided for circulating cooled fluid from the second chamber into the third chamber via the fluid pathways. For example, when the temperature sensor senses that the temperature within the third chamber has risen above a certain predetermined range, it outputs a signal which opens the shutter mechanisms and activates the fan. Additionally, a heater may be provided. For example, when the temperature sensor senses that the temperature within the third chamber has dropped below a predetermined range, the temperature sensor outputs a signal that activates the heater to raise the temperature within the third chamber. A time and temperature monitoring apparatus may be provided within the container for recording the temperature history of the time during which the material is being stored and/or transported.

The apparatus according to another embodiment of the invention includes inner and outer shells. The inner shell is so disposed so disposed as to form a first chamber between the outer shell and the inner shell and a second chamber for receiving therein a material for storage and/or transport. An insulation layer is disposed within the first chamber and is preferably sealed within the first chamber. Either a filler material pre-chilled in a cryogenic fluid and/or a pre-charged cryogenic material insert is disposed within the second chamber so as to maintain the temperature within the second chamber within a predetermined range. A lid is provided for sealing a material for storage and/or transport within the apparatus.

The inner and outer shells are preferably each formed of a material having low thermal conductivity and high resistivity to low temperatures. The insulation layer is preferably formed of at least one layer of aerogel disposed with a layer of metalized polyethylene. The insulation layer is preferably sealed within the first chamber by a sealing member. The insulation layer may further include a getter material.

Where the apparatus contains an insert that contains a phase change material disposed within the second chamber fluid, the phase change material may include cut-outs for receiving therein a cryogenic material. The phase change material may contain a heat conductive material. Where a filler material pre-chilled in a cryogenic fluid is disposed within the second chamber, the filler material may be polyethylene beads.

The apparatus may also include pressure and temperature monitoring apparatus for recording temperature history while a material is being stored and/or transported in said container.

The apparatus may also include a vacuum valve having ports in fluid communication with the first and second chambers, the vacuum valve being connectable to a vacuum pump for evacuating air from the first and second chambers.

The lid is preferably formed of a rigid polyurethane foam reinforced with s-glass, and may include a collar portion, which seals the first chamber, and a top portion, which seals the second chamber. The collar portion and top portion may be sealed together by two sealing members.

Preferred embodiments for the invention are discussed below with reference to the drawings.

Figure 1:
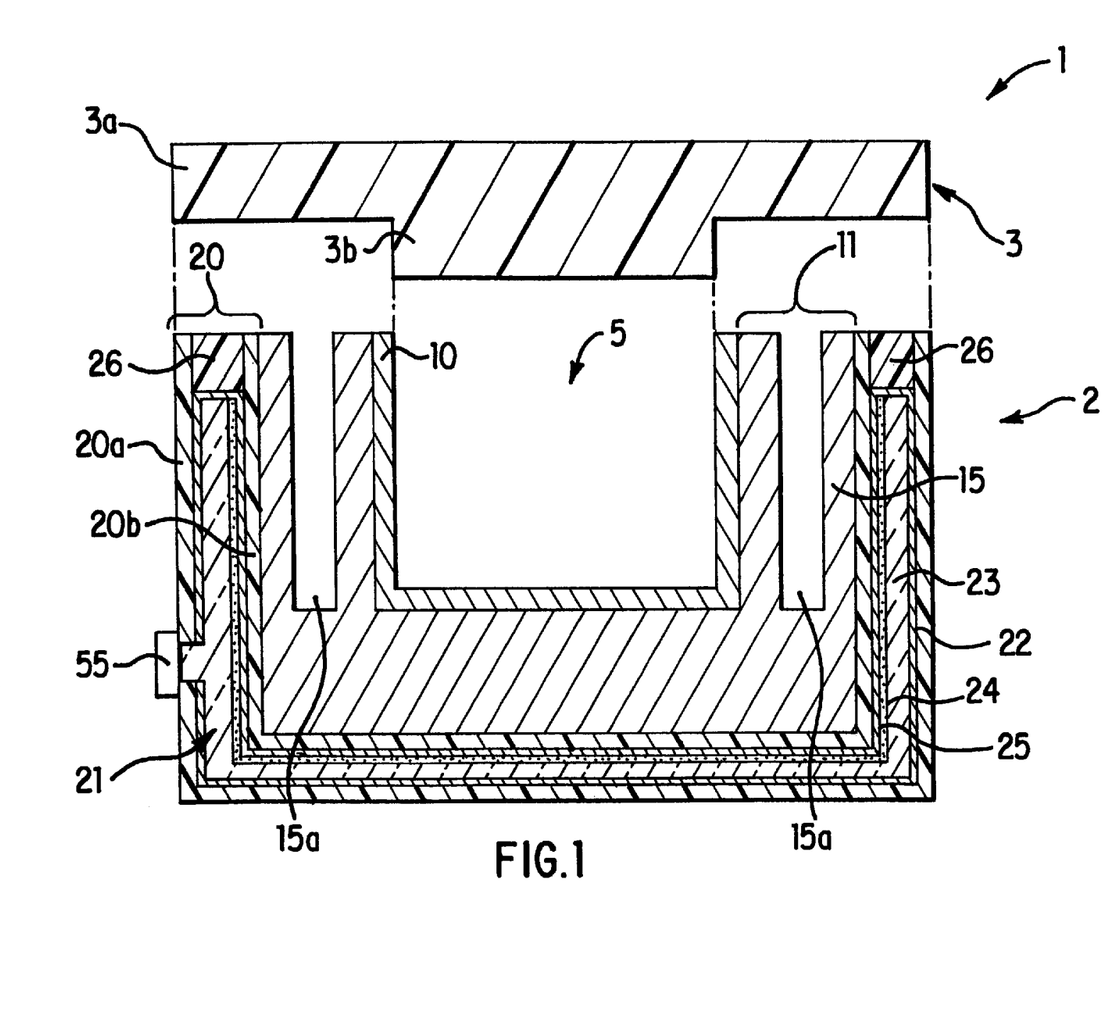
FIG. 1 is a cross-sectional view of a container according to the invention.
Figure 2:
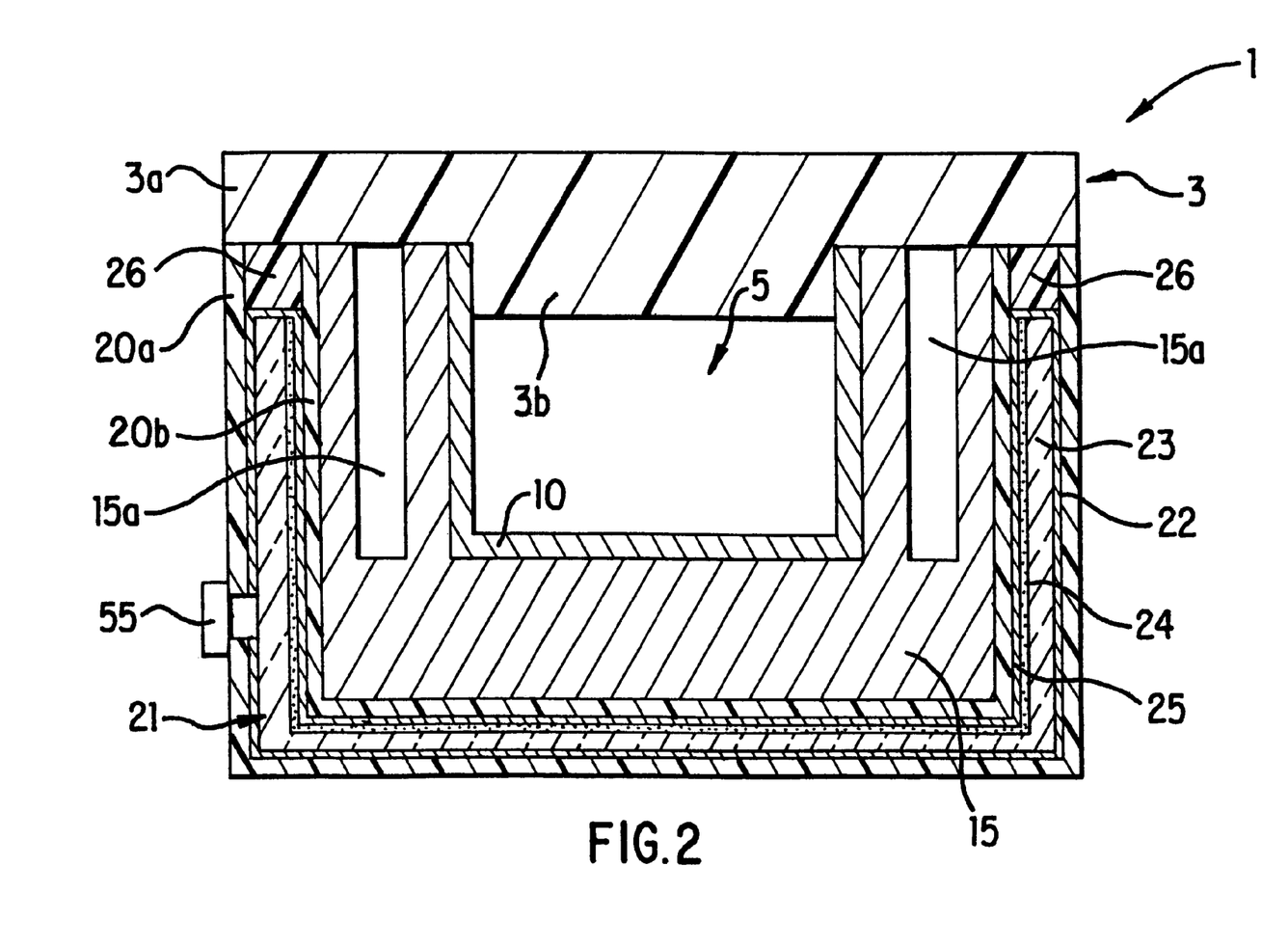
FIG. 2 is a cross-sectional view of the closed container of FIG. 1.

An apparatus 1 for storing and/or transporting material 90, such as biological samples, tissues and/or organs, is shown in FIGS. 1–2. The apparatus includes a container 2 having an inner shell 10 and an outer shell 20. When the container 2 is assembled, the inner shell 10 is disposed within the outer shell 20. The inner shell 10 and the outer shell 20 are preferably three dimensionally rectangular in shape; however, other shapes, such as, for example, cylindrical or polyhedral, may also be appropriate. The inner shell 10 forms a chamber 5 for receiving therein a material 90 to be stored and/or transported.

The outer shell 20 is formed of outer and inner shell members 20a, 20b. The outer and inner shell members 20a, 20b of the outer shell 20 are preferably formed of a material having low thermal conductivity and high resistivity to low temperature and high pressure, such as a carbon/epoxy composite or e-glass; however, other materials are also appropriate. A chamber 20c is formed between the outer and inner shell members 20a, 20b.

Disposed within the inner shell member 20b is a multi-layer of insulation 21. The insulation layer 21 preferably includes a layer of aerogel 23, such as, for example, silica aerogel, alumina aerogel, zirconia aerogel, carbon aerogel, boron aerogel, tungsten aerogel, titania aerogel, aerogel made by the sol-gel polymerization of resorcinol with formaldehyde, and aerogel made by the sol-gel polymerization of melamine with formaldehyde, disposed within a layer 22 of metalized polyethylene. Because of the porous nature of aerogels, aerogels achieve low rates of heat transmission, and do not lose strength when subjected to vacuum pressure. In each of the embodiments discussed herein, the aerogel combined with the applied vacuum and the other structure results in an improved insulation or "R" value. For example, for a particular aerogel, using a vacuum of about 29 inches or more of water, e.g., 29.9 inches, the insulation value increases four or five fold.

The metalized polyethylene layer provide low permeability to most gases, possess some elasticity and resist cracking at low temperatures. It is preferably formed of gold metalized MYLAR brand polyethylene. A getter material (shown at 24 in FIGS. 1–2) may also be provided. The getter material may be any conventional material that absorbs trace gases within a vacuum, such as, for example, titanium, sodium, potassium, magnesium, calcium, strontium, barium, cesium-rubidium alloys, tantalum, zirconium and rare-earth elements, such as, hafnium. The chamber 20c is sealed by a sealing member 26. The sealing member 26 is preferably formed of a phenolic microballoon epoxy. A vacuum port 55 is formed in the outer shell member 20a to allow a vacuum source to be connected to the chamber 20c formed between the outer and inner shell members 20a, 20b to evacuate chamber 20c. Port 55 is sealable to maintain the vacuum when the vacuum source is detached.

A chamber 11 is formed between the outer and inner shells 10, 20. A phase change material 15 is disposed within the chamber 11. The phase change material is any material which changes from a solid to a liquid state at a substantially constant temperature. The phase change material is preferably paraffin wax; however, other phase change materials, such as, for example, lithium chloride, n-tetradecane, 1-decanol, n-pentadecane, chloroacetic acid-o-cresol eutestic, tetradecylbenzene, sodium chromate decahydrate, n-octanoic acid, chloroacetic acid-phenol eutectic, acetic acid, salt mixture of 37% $NaSO_4$, 17% $NaCl$ and 46% $H_2O$, 1-octadecene, glycerol, n-hexadecane, polyethylene glycol 600, double clathrate of water with tetrahydrofuran and hydrogen sulfide, lithium chloride ethanolate, n-heptadecane, copper nitrate hexahydrate, lactic acid, manganous nitrate hexahydrate, n-octadecane, methyl palmitate, 3-methylpentacosane, orthophosphoric acid hemihydrate, lithium nitrate trihydrate, calcium chloride hexahydrate, gallium, sodium sulfate decahydrate, levulinic acid, n-eicosane, Sun Wax P-116, or another similar material may also be appropriate. The phase change material 15 is frozen by introducing a compressed cryogenic material, such as, for example, solid carbon dioxide or liquid nitrogen, into cut-outs 15a provided in the phase change material and allowing the cryogenic material to expand. To increase the effectiveness of the phase change material 15, that is, to increase the speed by which the material changes phase, heat conductive material such as aluminum oxide powder may be added thereto.

A lid 3 is provided to seal the container 2, thereby sealing the material 90 placed in the chamber 5 within the container 2. The lid 3 includes a top portion 3a and an inner portion 3b, which is capable of sealing the inner shell 10 and, thus, the chamber 5. The lid 3 is preferably formed of a phenolic/microballoon epoxy; however, other materials may also be appropriate for the lid 3. Lid 3 may also seal the chamber 11.

The components of this embodiment and of the remaining embodiments discussed herein are glued together where appropriate using known cryogenic adhesives or epoxy, that is, an adhesive especially designed to resist shrinkage when exposed to low temperatures.

In use, a cryogenic material is introduced into the cut-outs 15a in the phase change material 15 disposed between outer and inner shells 10, 20, freezing the phase change material 15. Next, a material 90 to be stored and/or transported within the apparatus 1 is placed within the chamber 5 of the inner shell 10. The lid 3 is then positioned to seal the container 2. Compressed cryogenic material may be allowed to fully expand before the container 2 is sealed, or alternatively, a vent to the ambient atmosphere may be provided in the lid 3 to allow gases to escape as the optionally compressed cryogenic material expands.

A vacuum pump (not shown) is connected to the port 55 to evacuate air from the chamber 20c between the outer and inner shell members 20a, 20b of the outer shell 20. The vacuum is preferably in the order of .01 to 1 torr. The vacuum pump is then withdrawn and port 55 is closed. The getter material absorbs any trace gases remaining in the vacuum space.

Figure 3:
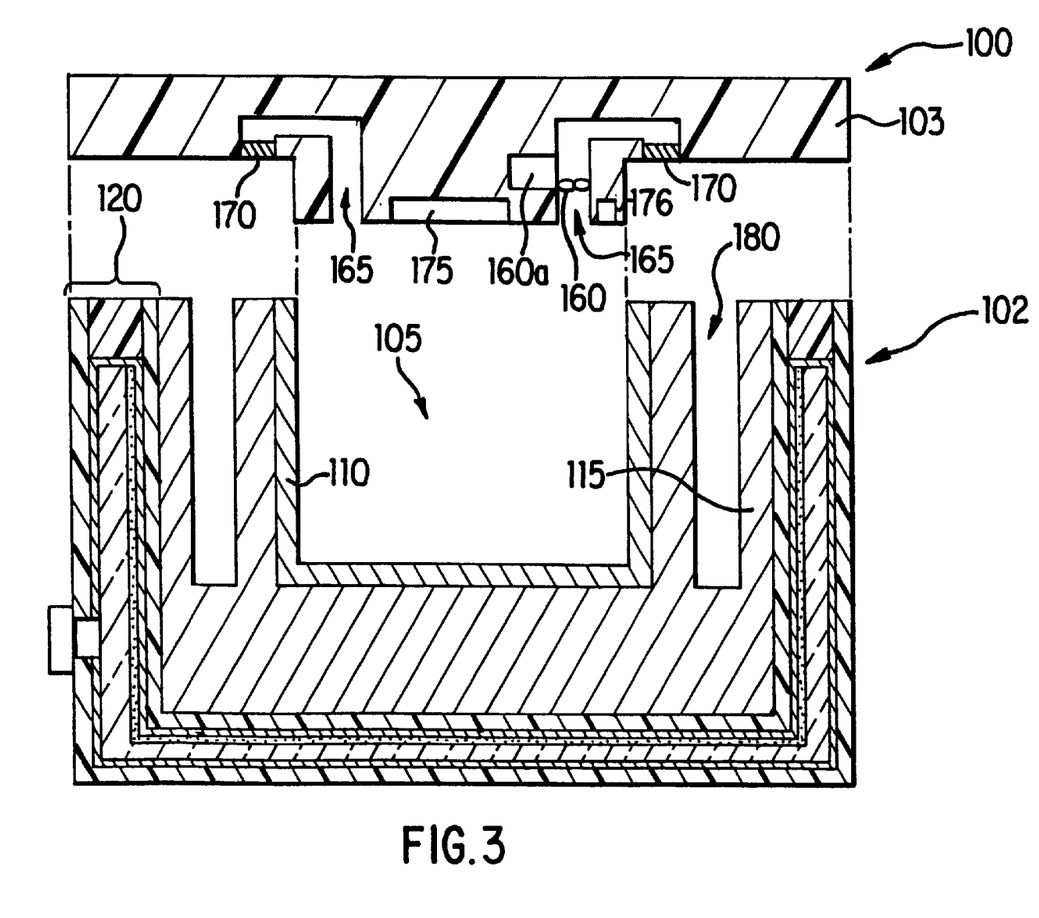
FIG. 3 is a cross-sectional view of an alternative container according to the invention.
Figure 4:
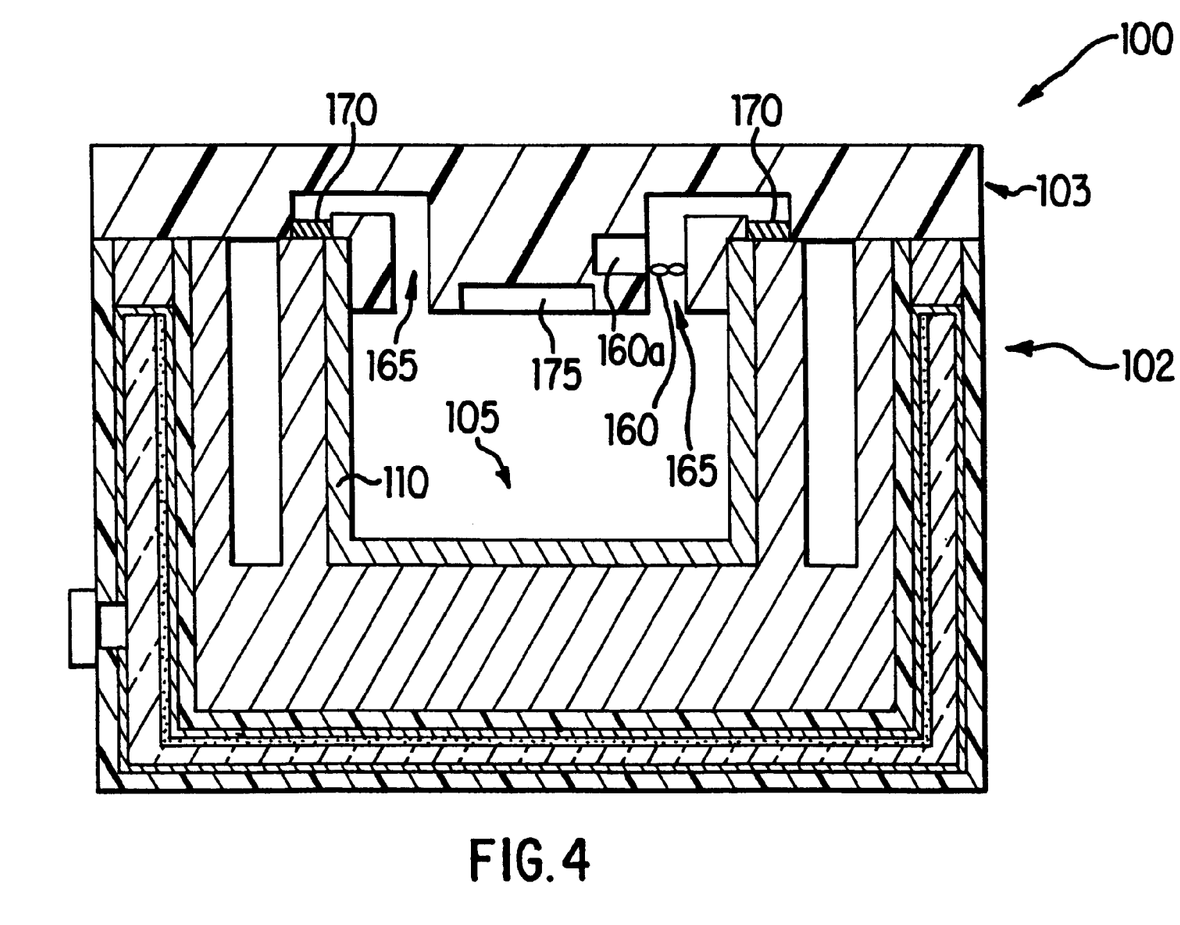
FIG. 4 is a cross-sectional view of the closed container of FIG. 3.

FIGS. 3–4 show another embodiment of the apparatus according to the invention. The embodiment of FIGS. 3–4 is similar to the embodiment of FIGS. 1–2. Repetitive discussion of like structure has been omitted. In FIGS. 3–4, like reference numerals have been used to depict like elements.

In the embodiment of FIGS. 3–4, the inner container 110 includes a gap 180 disposed between the inner shell 110 and the phase change material 115. Air or other gas, e.g. inert gas, within the gap 180 is cooled by the adjacent phase change material. A lid 103 is provided to seal the container 102 thereby sealing the material placed in the chamber 105 within the container 102. The embodiment of FIGS. 3–4 further includes a heater 175, a fan 160 (with motor 160a), shutter mechanisms 170, 170 and a temperature sensor 176, all preferably disposed within the lid 103, utilized to control the temperature within the chamber 105. In response to signals from the temperature sensor 176, the shutter mechanisms 170, 170 are opened, and the fan 160 circulates the cooled gas from the gap 180 into the chamber 105 to reduce the temperature within the chamber 105. Alternatively, the heater 175 is activated to raise the temperature within the chamber 105. The fan motor 160a may be insulated or magnetic and preferably is configured not to conduct heat to the cooled gas being circulated.

With such apparatus, the invention is capable of maintaining the temperature within the chamber 105 within a predetermined range capable of preserving the material disposed within the chamber 105. Further, the apparatus may include time and temperature monitoring and recording apparatus (not shown) for recording the temperature history of the time during which the material is being stored and/or transported.

Figure 5:
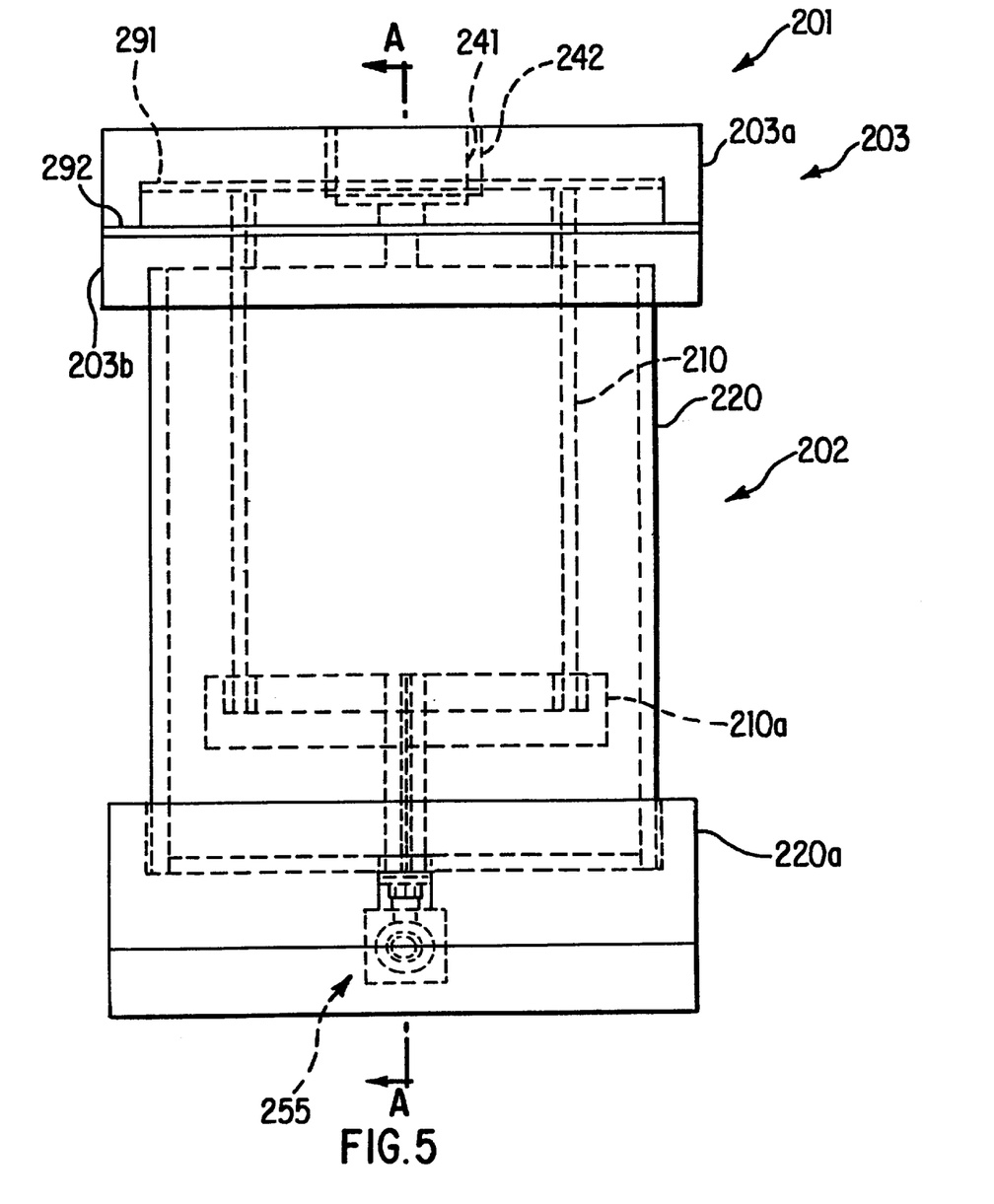
FIG. 5 is a side view of another alternative container according to the invention.
Figure 6:
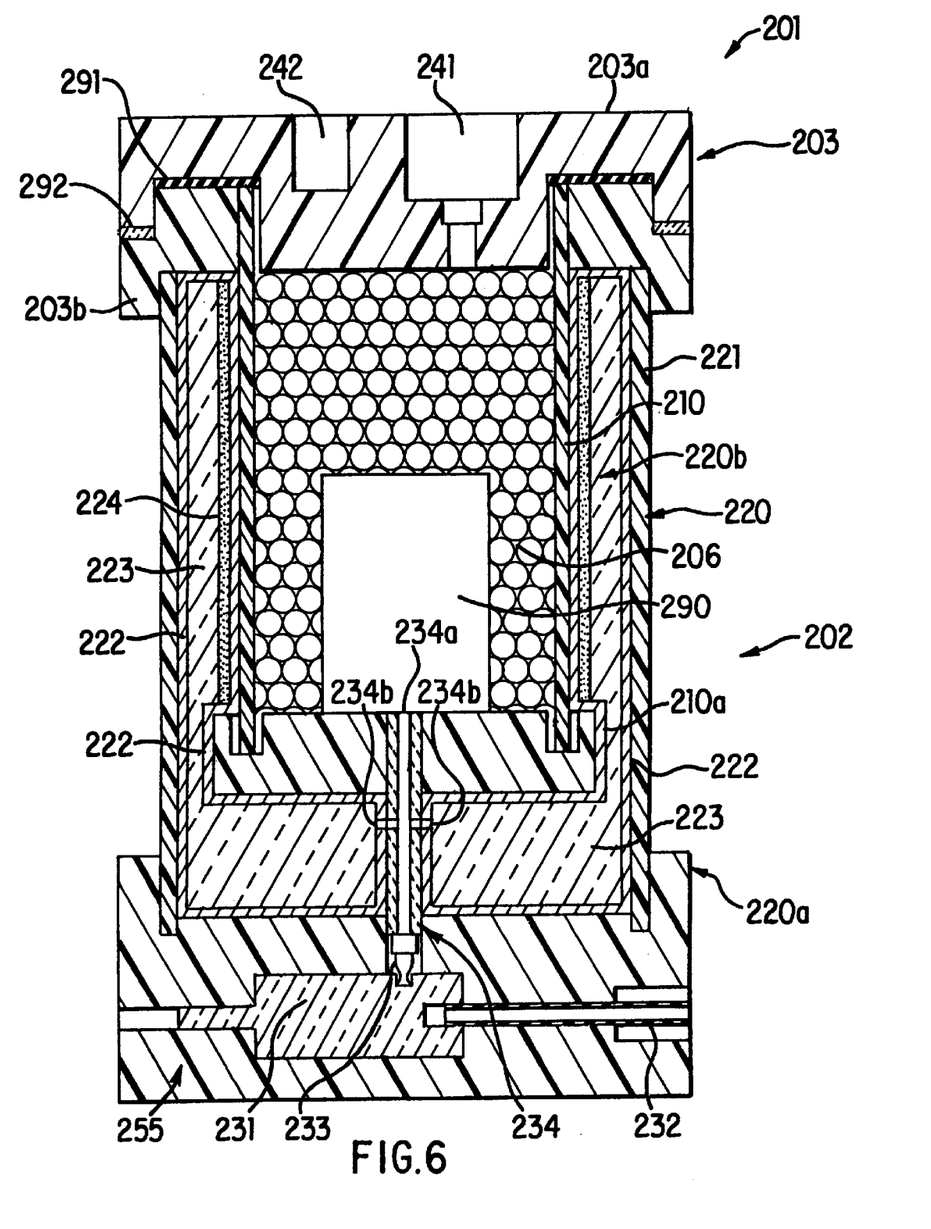
FIG. 6 is a cross-sectional view of the container of FIG. 5 taken along line AA.
Figure 7:
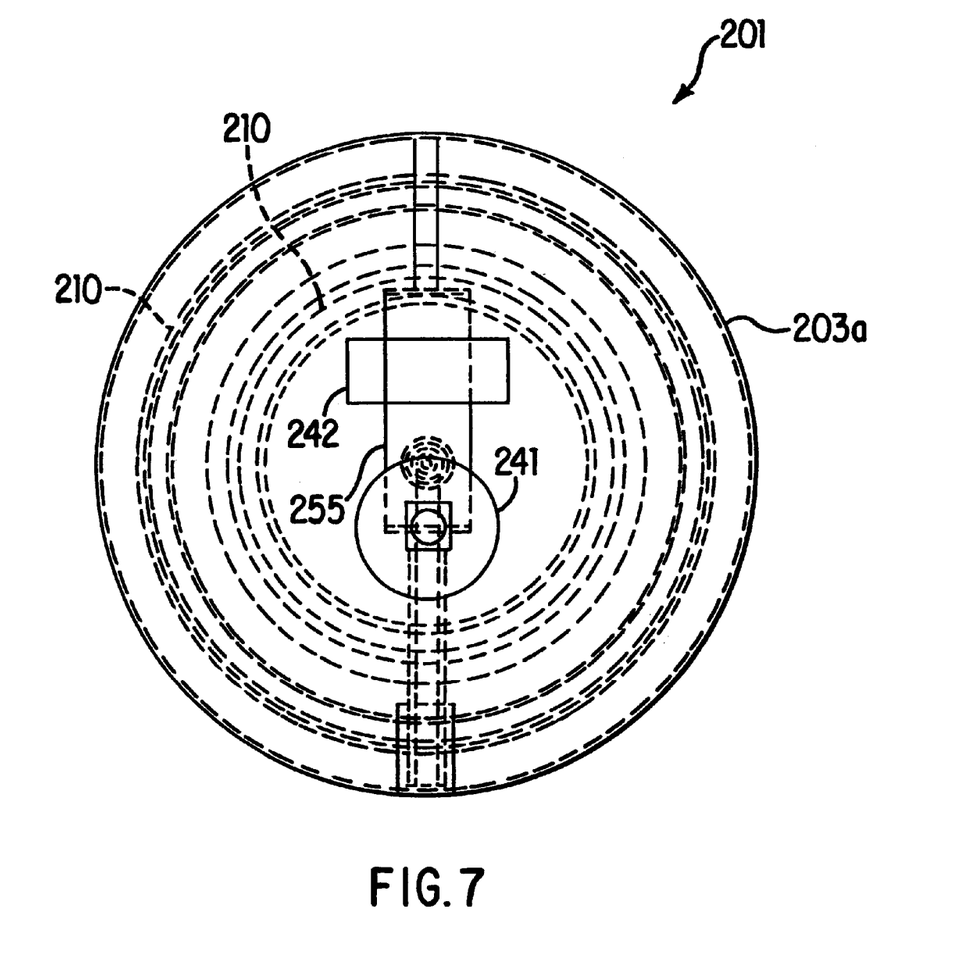
FIG. 7 is a top view of the container of FIG. 5.

FIGS. 5–7 show another embodiment of the apparatus according to the invention. The embodiment of FIGS. 5–7 is similar to the embodiment of FIGS. 1–4; however, in the embodiment of FIGS. 5–7 a filler material 206 is utilized to maintain the material 290 to be stored and/or transported at a temperature sufficient to preserve the material 290. Repetitive discussion of like structure has been omitted. In FIGS. 5–7, like reference numerals have been used to depict like elements.

The apparatus 201 for storing and/or transporting material 290, such as biological samples, tissues and/or organs, shown in FIGS. 5–7, includes a container 202 having an inner shell 210 and an outer shell 220. When the apparatus 201 is assembled, the inner shell 210 is disposed within the outer shell 220 to form a chamber 220b therebetween. Each of the inner and outer shells 210, 220 has a base 210a, 220a.

The inner shell 210 and the outer shell 220 are preferably cylindrical in shape; however, other shapes, such as, for example, three dimensionally rectangular or polyhedral, may also be appropriate. The inner shell 210 forms a chamber 205 for receiving therein a material 290 to be stored and/or transported.

The outer shell 220 is preferably formed of a material having low thermal conductivity and high resistivity to low temperature and high pressure, such as a carbon/epoxy composite or e-glass; however, other materials are also appropriate. The base 220a is preferably formed of a rigid polyurethane foam reinforced with s-glass epoxy; however, other materials are also appropriate.

Disposed within the chamber 220b is a multi-layer of insulation 221. The insulation layer 221 preferably includes a layer of aerogel 223, such as, for example, any of the aerogels previously discussed, disposed within a layer 222 of metalized polyethylene. As previously discussed, aerogels achieve low rates of heat transmission, and do not lose strength when subjected to vacuum pressure while the metalized polyethylene layer, preferably gold metalized MYLAR brand polyethylene, provides low permeability to most gases, possess some elasticity and resist cracking at low temperatures. A getter material 224 may also be provided. The getter material may be any conventional material that absorbs trace gases within a vacuum, such as, for example, any of such materials previously discussed.

The inner shell 210 is preferably formed of a material having a low thermal conductivity and high resistivity to low temperatures, such as, for example, s-glass; however, other materials are also appropriate. The base 210a is preferably formed of a rigid polyurethane foam reinforced with s-glass; however, other materials are also appropriate. A filler material 206, which has been stored in a cryogenic material, is packed into the chamber 205 after a material 290 to be stored and/or transported is placed within the chamber 205. The filler material 206 is preferably polyethylene beads. In this embodiment, there is no outgassing or cryogenic liquids that interfere with the vacuum. However, a filler material may also be used with any of the other embodiments of the invention discussed herein to provide additional cooling and packing functions.

A lid 203 is provided to seal the chambers 205 and 220b, thereby sealing the material placed in the chamber 205 within the apparatus 201. The lid 203 includes a top portion 203a, which seals the chamber 205, and a collar portion 203b, which seals the chamber 220b. The collar portion may be sealed to the container 202 prior to use, or may be sealed to the container 202 during use, using an appropriate adhesive or cryoseal (not shown). The lid 203 is preferably formed of a rigid polyurethane foam reinforced with s-glass; however, other materials may also be appropriate for the lid 203. The top portion 203a is joined to the collar portion 203b using first and second cryoseals 291, 292. The first cryoseal 203a is preferably silicon rubber while the second cryoseal is preferably a closed cell foam; however, other materials are appropriate for either cryoseal.

Provided in the lid 203 are a pressure sensor 241, which monitors the pressure within the apparatus 201, and a temperature sensor 242, which monitors the temperature within the apparatus 201.

The base 220b is provided with a commercially available vacuum valve 255. The vacuum valve 255 includes a valve 231; a first tube 232, a fitting 233 and a second tube 234. The first tube 232 is preferably rubber and allows connection to an appropriate vacuum pump (not shown). The second tube 234 is preferably a material having low thermal conductivity, such as, for example, ceramic, and is connected to chambers 205 and 220b by a main port 234a and two side ports 234b. However, other material are appropriate for either tube. The application of the vacuum to both chambers 205, 220b increases the insulation valve of the aerogel decreasing the thermal conductivity within and from the apparatus 201.

In use, a material 290 to be stored and/or transported within the apparatus 201 is placed within the chamber 205. Next, the filler material 206, which has been stored in a cryogenic material, is packed around the material 290, and the lid 203 is put in place to seal both chambers 205 and 220b. Finally, the vacuum valve 55 is connected to an appropriate vacuum pump to evacuate air from both of the chambers 205 and 220b. The vacuum is preferably on the order of, for example, 0.01 to 1 torr. The vacuum pump is then withdrawn and the vacuum valve 255 closed. The getter material absorbs any trace gases remaining in the chamber 205.

Figure 8:
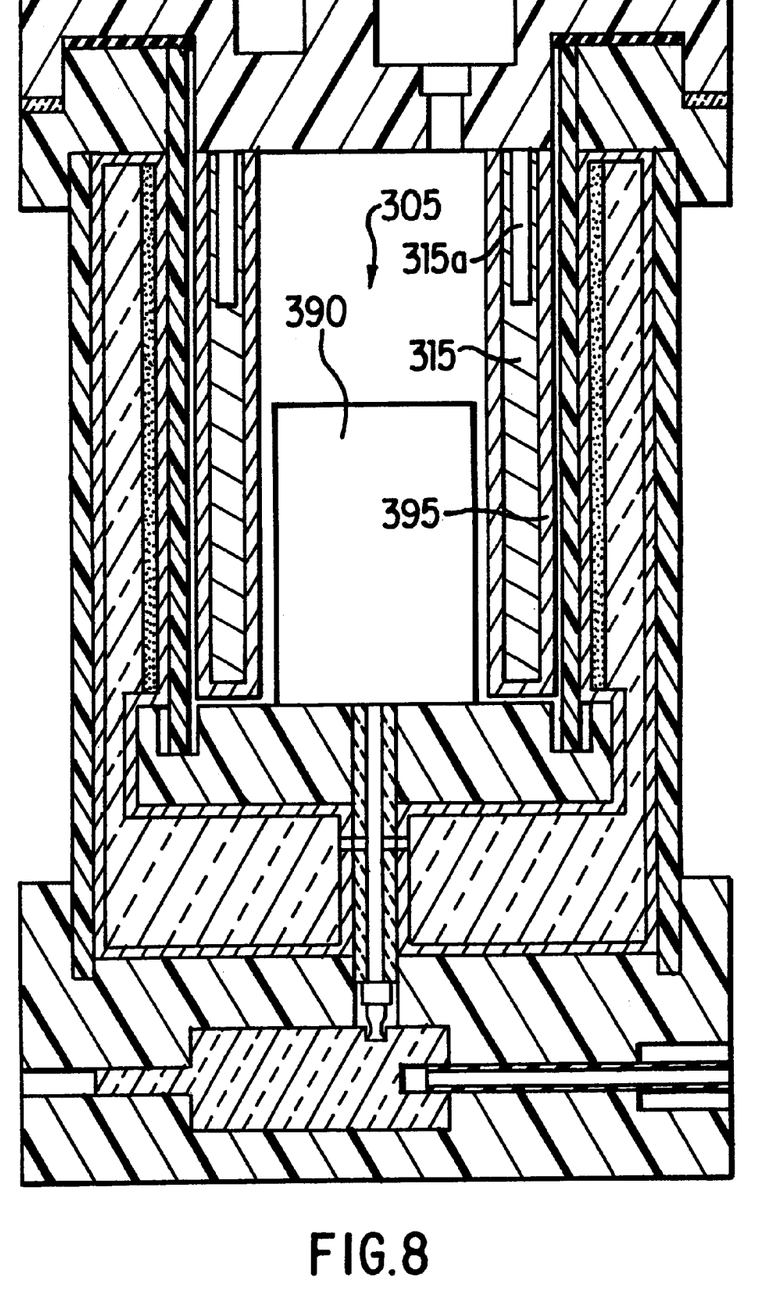
FIG. 8 is a cross-sectional view of another alternative container according to the invention.

FIG. 8 shows another embodiment of the apparatus according to the invention. The embodiment of FIG. 8 is similar to the embodiment of FIGS. 5–7; however, in the embodiment of FIG. 8 a phase change material insert 395 is provided in the chamber 305 and is utilized to maintain the material 390 to be stored and/or transported at a temperature sufficient to preserve the material. The phase change insert 395 can be used alone or along with the filler material previously discussed. Repetitive discussion of like structure has been omitted. In FIG. 8, like reference numerals have been used to depict like elements.

The phase change material insert 395 is preferably formed of a material having a high thermal conductivity and high resistivity to low temperatures, such as, for example, aluminum oxide epoxy, aluminum or stainless steel; however, other materials are also appropriate. The phase change material insert 395 forms a chamber 395a, which maybe open or sealed. A phase change material 315 is disposed within the chamber 395a. The phase change material is any material which changes from a solid to a liquid state at a substantially constant temperature. The phase change material 315 is preferably paraffin wax; however, other phase change materials, such as, for example, lithium chloride, n-tetradecane, 1-decanol, n-pentadecane, chloroacetic acid-o-cresol eutestic, tetradecylbenzene, sodium chromate decahydrate, n-octanoic acid, chloroacetic acid-phenol eutectic, acetic acid, salt mixture of 37% $NaSO_4$, 17% NaCl and 46% $H_2O$, 1-octadecene, glycerol, n-hexadecane, polyethylene glycol 600, double clathrate of water with tetrahydrofuran and hydrogen sulfide, lithium chloride ethanolate, n-heptadecane, copper nitrate hexahydrate, lactic acid, manganous nitrate hexahydrate, n-octadecane, methyl palmitate, 3-methylpentacosane, orthophosphoric acid hemihydrate, lithium nitrate trihydrate, calcium chloride hexahydrate, gallium, sodium sulfate decahydrate, levulinic acid, n-eicosane, Sun Wax P-116, or another similar material may also be appropriate. The phase change material 315 is either frozen by storage in a cryogenic material or an appropriate refrigeration device prior to use, or by introducing a compressed cryogenic material, such as, for example, solid carbon dioxide or liquid nitrogen, into optional cut-outs 315a provided in the phase change material and allowing the cryogenic material to expand within the insert. To increase the effectiveness of the phase change material 315, that is, to increase the speed by which the material changes phase, heat conductive material such as aluminum oxide powder may be added thereto.

Accordingly, the present invention provides a passive or active, long term storage capability for material, such as biological samples, tissues and/or organs that require low temperature for preservation. The apparatus substantially eliminates heat leak, while providing low temperatures.

While the invention has been described in conjunction with specific embodiments thereof, it is evident that many alternatives, modifications and variations may be apparent to those skilled in the art. Accordingly, the preferred embodiments of the invention as set forth herein is intended to be illustrative, not limiting. Various changes may be made without departing from the spirit and scope of the invention as defined in the following claims.

What is claimed is:

1. An apparatus comprising:
   an outer shell comprising inner and outer shell members having a first chamber formed therebetween, the inner and outer shell members being formed of a material having low thermal conductivity and high resistivity to low temperature;
   an insulation layer disposed within the first chamber, the insulation layer being sealed within the first chamber;
   an inner shell so disposed as to form a second chamber between the outer shell and the inner shell, the inner shell being formed of a material having high thermal conductivity and high resistivity to low temperature;
   a phase change material disposed within the second chamber, the phase change material having cut-outs for receiving therein a cryogenic material;
   a third chamber formed by the inner shell for receiving therein a material for storage and/or transport; and
   a lid for sealing a material for storage and/or transport within the apparatus.

2. The apparatus according to claim 1, wherein the lid seals the cryogenic material within the second chamber.

3. The apparatus according to claim 2, wherein the insulation layer is formed of at least one layer of aerogel disposed within a layer of metalized polyethylene.

4. The apparatus according to claim 3, wherein the inner shell is formed of aluminum oxide epoxy, aluminum or stainless steel and the outer and inner shell members of the outer shell are formed of a carbon/epoxy composite.

5. The apparatus of claim 1, wherein the insulation layer is sealed within the first chamber by a sealing member.

6. The apparatus according to claim 1, wherein the phase change material is at least one member selected from the group consisting of paraffin wax, lithium chloride, n-tetradecane, 1-decanol, n-pentadecane, chloroacetic acid-o-cresol eutectic, tetradecylbenzene, sodium chromate decahydrate, n-octanoic acid, chloroacetic acid-phenol eutectic, acetic acid, salt mixture of 37% $NaSO_4$, 17% NaCl and 46% $H_2O$, 1-octadecene, glycerol, n-hexadecane, polyethylene glycol 600, double clathrate of water with tetrahydrofuran and hydrogen sulfide, lithium chloride ethanolate, n-heptadecane, copper nitrate hexahydrate, lactic acid, manganous nitrate hexahydrate, n-octadecane, methyl palmitate, 3-methylpentacosane, orthophosphoric acid hemihydrate, lithium nitrate trihydrate, calcium chloride hexahydrate, gallium, sodium sulfate decahydrate, levulinic acid and n-eicosane.

7. The apparatus according to claim 1, wherein the phase change material contains a heat conductive material.

8. The apparatus according to claim 3, wherein the aerogel is at least one member selected from the group consisting of silica aerogel, alumina aerogel, zirconia aerogel, carbon aerogel, boron aerogel, tungsten aerogel, titania aerogel, aerogel made by the sol-gel polymerization of resorcinol with formaldehyde, and aerogel made by the sol-gel polymerization of melamine with formaldehyde.

9. The apparatus according to claim 3, wherein the insulation layer further comprises a getter material.

10. The apparatus according to claim 1, wherein the inner and outer shells are three-dimensionally rectangular in shape.

11. The apparatus according to claim 1, further comprising time and temperature monitoring apparatus for recording temperature history while a material is being stored and/or transported in said container.

12. The apparatus according to claim 1, further comprising a vacuum port in fluid communication with the first chamber, the vacuum port being connectable to a vacuum pump for evacuating air from the first chamber.

13. The apparatus according to claim 1, wherein the lid is formed of a phenolic microballoon epoxy.

14. The apparatus according to claim 1, further comprising a gap disposed within the second chamber between the phase change material and the inner shell.

15. The apparatus according to claim 14, further comprising:
 a fluid pathway disposed in the lid and allowing fluid communication between the gap within the second chamber and the third chamber, the fluid pathway having a shutter mechanism;
 a temperature sensor within the third chamber;
 a fan configured to circulate fluid between the gap and the third chamber, wherein when the temperature sensor senses that the temperature within the third chamber has risen above a certain predetermined range, the temperature sensor outputs a signal which opens the shutter mechanism and activates the fan to circulate cooled fluid from the gap into the third chamber.

16. The apparatus according to claim 15, further comprising a heater, wherein when the temperature sensor senses that the temperature within the third chamber has dropped below a predetermined range, the temperature sensor outputs a signal that activates the heater to raise the temperature within the third chamber.

17. An apparatus comprising:
 containing means for containing therein a material for storage and/or transport, the containing means comprising an inner shell disposed within an outer shell, the inner shell being formed of a material having high thermal conductivity and high resistivity to low temperature and the outer shell being formed of inner and outer shell members formed of a material having low thermal conductivity and high resistivity to low temperature and having a first chamber formed therebetween;
 insulating means for insulating the outer shell, the insulating means being disposed within the first chamber;
 phase change means for cooling a material contained within the containing means, the phase change means being disposed within a second chamber formed between the inner and outer shells and having cut-outs for receiving therein a cryogenic material to freeze or charge the phase change means; and
 sealing means for sealing a material for storage and/or transport within a third chamber formed by the inner shell of the containing means.

18. The apparatus according to claim 17, further comprising a gap disposed within the second chamber between the phase change material and the inner shell.

19. The apparatus according to claim 18, further comprising:
 fluid pathway means for allowing fluid communication between the gap within the second chamber and the third chamber;
 sensor means for sensing the temperature within the third chamber;
 circulation means for circulating fluid between the gap and the third chamber when the sensor means senses that the temperature within the third chamber has risen above a certain predetermined range.

20. The apparatus according to claim 19, further comprising heater means for raising the temperature within the third chamber when the sensor means senses that the temperature within the third chamber has dropped below a predetermined range.

21. A method of preserving a material during storage and/or transport, the method comprising:
 placing a material for storage and/or transport in a container comprising:
  an inner shell disposed within an outer shell, the inner shell being formed of a material having high thermal conductivity and high resistivity to high temperature and the outer shell being formed of inner and outer shell members formed of a material having low thermal conductivity and high resistivity to low temperature and having a first chamber formed therebetween;
  an insulation layer disposed within the first chamber; and
  a phase change material disposed within a second chamber formed between the inner and outer shells;
 freezing or charging the phase change material by placing a cryogenic material into cutouts formed in the phase change material;
 applying a vacuum to the first chamber; and
 sealing the material for storage and/or transport within a third chamber formed by the inner shell.

22. The method according to claim 21, wherein the material for storage and/or transfer is a biological sample.

23. The method according to claim 21, wherein the material for storage and/or transfer is a tissue or organ.

24. The method according to claim 21, wherein the cryogenic material is compressed and expands in the cutouts.

25. The method according to claim 21, wherein the cryogenic material is solid carbon dioxide.

26. The method according to claim 21, wherein the cryogenic material is liquid nitrogen.

27. The method according to claim 21, wherein the container further comprises a gap disposed within the second chamber between the phase change material and the inner shell.

28. The method according to claim 27, further comprising:
 selectively allowing fluid communication between the gap within the second chamber and the third chamber;
 sensing the temperature within the third chamber;
 circulating fluid between the gap and the third chamber when the temperature within the third chamber has risen above a certain predetermined range.

29. The apparatus according to claim 28, further comprising:
 heating the air within the third chamber to raise the temperature within the third chamber when the temperature within the third chamber has dropped below a predetermined range.

30. An apparatus comprising:
- an outer shell formed of a material having low thermal conductivity and high resistivity to low temperature;
- an inner shell formed of a material having low thermal conductivity and high resistivity to low temperature and so disposed as to form a first chamber between the outer shell and the inner shell and a second chamber for receiving therein a material for storage and/or transport;
- an insulation layer disposed within the first chamber, the insulation layer being sealed within the first chamber;
- at least one of a filler material disposed within the second chamber pre-chilled in a cryogenic fluid and an insert that contains a phase change material disposed within the second chamber pre-charged with a cryogenic fluid so as to maintain the temperature within the second chamber within a p redetermined range; and
- a lid for sealing a material for storage and/or transport within the apparatus.

31. The apparatus according to claim 30, wherein the insulation layer is formed of at least one layer of aerogel disposed within a layer of metalized polyethylene.

32. The apparatus of claim 30, wherein the insulation layer is sealed within the first chamber by a sealing member.

33. The apparatus according to claim 31, wherein the aerogel is at least one member selected from the group consisting of silica aerogel, alumina aerogel, zirconia aerogel, carbon aerogel, boron aerogel, tungsten aerogel, titania aerogel, aerogel made by the sol-gel polymerization of resorcinol with formaldehyde, and aerogel made by the sol-gel polymerization of melamine with formaldehyde.

34. The apparatus according to claim 31, wherein the insulation layer further comprises a getter material.

35. The apparatus according to claim 30, comprising an insert that contains a phase change material disposed within the second chamber so as to maintain the temperature within the second chamber within a predetermined range.

36. The apparatus according to claim 35, wherein the lid seals the insert and the material for storage and/or transport within the second chamber.

37. The apparatus according to claim 35, wherein the phase change material has cut-outs for receiving therein a cryogenic material.

38. The apparatus according to claim 35, wherein the phase change material is at least one member selected from the group consisting of paraffin wax, lithium chloride, n-tetradecane, 1-decanol, n-pentadecane, chloroacetic acid-o-cresol eutectic, tetradecylbenzene, sodium chromate decahydrate, n-octanoic acid, chloroacetic acid-phenol eutectic, acetic acid, salt mixture of 37% $NaSO_4$, 17% $NaCl$ and 46% $H_2O$, 1-octadecene, glycerol, n-hexadecane, polyethylene glycol 600, double clathrate of water with tetrahydrofuran and hydrogen sulfide, lithium chloride ethanolate, n-heptadecane, copper nitrate hexahydrate, lactic acid, manganous nitrate hexahydrate, n-octadecane, methyl palmitate, 3-methylpentacosane, orthophosphoric acid hemihydrate, lithium nitrate trihydrate, calcium chloride hexahydrate, gallium, sodium sulfate decahydrate, levulinic acid and n-eicosane.

39. The apparatus according to claim 38, wherein the phase change material contains a heat conductive material.

40. The apparatus according to claim 30, further comprising pressure and temperature monitoring apparatus for recording temperature history while a material is being stored and/or transported in said container.

41. The apparatus according to claim 30, further comprising a vacuum valve having ports in fluid communication with the first and second chambers, the vacuum valve being connectable to a vacuum pump for evacuating air from the first and second chambers.

42. The apparatus according to claim 30, comprising a filler material disposed within the second chamber pre-chilled in a cryogenic fluid so as to maintain the temperature within the second chamber within a predetermined range.

43. The apparatus according to claim 42, wherein the filler material is polyethylene beads.

44. The apparatus according to claim 42, wherein the lid seals the filler material and the material for storage and/or transport within the second chamber.

45. The apparatus according to claim 30, comprising a filler material disposed within the second chamber pre-chilled in a cryogenic fluid and an insert that contains a phase change material disposed within the second chamber pre-charged with a cryogenic fluid so as to maintain the temperature within the second chamber within a predetermined range.

46. The apparatus according to claim 30, wherein the lid is formed of a rigid polyurethane foam reinforced with s-glass.

47. The apparatus according to claim 30, wherein the lid is formed of a collar portion, which seals the first chamber, and a top portion, which seals the second chamber.

48. The apparatus according to claim 30, wherein the collar portion and top portion are sealed together by two sealing members.

49. A method of preserving a material during storage and/or transport, the method comprising:
- placing a material for storage and/or transport in a container comprising:
  - an outer shell formed of a material having low thermal conductivity and high resistivity to low temperature;
  - an inner shell formed of a material having low thermal conductivity and high resistivity to low temperature and so disposed as to form a first chamber between the outer shell and the inner shell and a second chamber for receiving therein a material for storage and/or transport;
  - an insulation layer disposed within the first chamber, the insulation layer being sealed within the first chamber; and
  - an insert that contains a phase change material disposed within the second chamber;
- freezing or charging the phase change material by one of storing the insert in a cryogenic material or refrigeration device prior to use and placing a cryogenic material into cutouts formed in the phase change material;
- applying a vacuum to the first and second chambers; and
- sealing the material for storage and/or transport within the second chamber.

50. A method of preserving a material during storage and/or transport, the method comprising:
- placing a material for storage and/or transport in a container comprising:
  - an outer shell formed of a material having low thermal conductivity and high resistivity to low temperature;
  - an inner shell formed of a material having low thermal conductivity and high resistivity to low temperature and so disposed as to form a first chamber between the outer shell and the inner shell and a second chamber for receiving therein a material for storage and/or transport; and
  - an insulation layer disposed within the first chamber, the insulation layer being sealed within the first chamber;

filling the second chamber with a filler material prechilled in a cryogenic material;

applying a vacuum to the first and second chambers; and sealing the material for storage and/or transport within the second chamber.

51. An apparatus comprising:

inner and outer shell members having a chamber formed therebetween, the inner and outer shell members being formed of a material having low thermal conductivity and high resistivity to low temperature, the inner shell member being configured to receive therein a material for storage and/or transport; and an insulation layer disposed within the chamber, the insulation layer being sealed within the chamber and being formed of at least one layer of aerogel disposed between two layers of metalized polyethylene.

52. The apparatus according to claim 51, wherein the outer and inner shell are formed of one of a carbon/epoxy composite and e-glass.

53. The apparatus according to claim 51, wherein the insulation layer further comprises a getter material.

54. The apparatus according to claim 51, further comprising a lid for sealing a material for storage and/or transport within the inner shell member.

55. The apparatus according to claim 51, wherein said insulation layer is evacuated to a vacuum of at least 29 inches of water.

56. The method according to claim 50, wherein said filler material is comprised of polyethylene beads.

57. The method according to claim 56, wherein said cryogenic material is liquid nitrogen.

58. The apparatus according to claim 1, wherein a cryogenic material is disposed within the cutouts of said phase change material.

59. The method according to claim 50, wherein the vacuum applied to the first and second chambers is attained by connecting a vacuum pump to a single vacuum valve.

60. The apparatus according to claim 17, wherein a cryogenic material is disposed within the cutouts of said phase change material.

* * * * *